US008858588B2

(12) United States Patent
Sigmon, Jr. et al.

(10) Patent No.: US 8,858,588 B2
(45) Date of Patent: Oct. 14, 2014

(54) MEDICAL DEVICES WITH DETACHABLE PIVOTABLE JAWS

(75) Inventors: John Crowder Sigmon, Jr., Greensboro, NC (US); Michelle D. Martinez, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 306 days.

(21) Appl. No.: 13/270,784

(22) Filed: Oct. 11, 2011

(65) Prior Publication Data

US 2012/0089176 A1 Apr. 12, 2012

Related U.S. Application Data

(63) Continuation-in-part of application No. 12/971,873, filed on Dec. 17, 2010.

(60) Provisional application No. 61/391,875, filed on Oct. 11, 2010.

(51) Int. Cl.
| | | |
|---|---|---|
| A61B 17/28 | (2006.01) | |
| A61B 17/10 | (2006.01) | |
| A61B 17/08 | (2006.01) | |
| A61B 17/128 | (2006.01) | |
| A61B 17/29 | (2006.01) | |
| A61B 17/12 | (2006.01) | |
| A61B 17/122 | (2006.01) | |
| A61B 17/00 | (2006.01) | |

(52) U.S. Cl.
CPC ............ *A61B 17/10* (2013.01); *A61B 17/1285* (2013.01); *A61B 17/29* (2013.01); *A61B 17/08* (2013.01); *A61B 2017/12004* (2013.01); *A61B 17/122* (2013.01); *A61B 2017/00473* (2013.01); *A61B 2017/2939* (2013.01); *A61B 2017/2944* (2013.01); *A61B 2017/2936* (2013.01); *A61B 2017/2931* (2013.01)

USPC .......................................... 606/205

(58) Field of Classification Search
CPC ............ A61B 7/08; A61B 7/10; A61B 7/122; A61B 7/128; A61B 7/1285; A61B 2017/00473; A61B 2017/2902; A61B 2017/2931; A61B 2017/2943; A61B 2017/294; A61B 2017/2944; A61B 2017/2916
USPC .............. 606/142, 205, 1, 139, 143, 206, 207
See application file for complete search history.

(56) References Cited

U.S. PATENT DOCUMENTS

| 720,385 A | 2/1903 | Storle |
|---|---|---|
| 2,614,445 A | 10/1952 | Riordan |

(Continued)

FOREIGN PATENT DOCUMENTS

| DE | 19534320 | 2/1997 |
|---|---|---|
| DE | 19750878 A1 | 5/1999 |

(Continued)

OTHER PUBLICATIONS

Office Action dated Nov. 6, 2013 U.S. Appl. No. 12/971,873 in related application.

(Continued)

*Primary Examiner* — Julian W Woo
*Assistant Examiner* — Shaun L David
(74) *Attorney, Agent, or Firm* — Brinks Gilson & Lione (57) ABSTRACT

Medical systems, devices and methods are provided for engaging tissue, e.g. for clipping tissue, closing a perforation or performing hemostasis. Generally, the medical system including a housing, first and second jaws rotatable relative to the housing, first and second links pivotally attached to the jaws, and a driver. The housing, first and second jaws, and first and second links form a linkage mechanism that allows the jaws to engage tissue and be left in vivo.

21 Claims, 8 Drawing Sheets

(56) References Cited

U.S. PATENT DOCUMENTS

| | | |
|---|---|---|
| 3,958,576 A | 5/1976 | Komiya |
| 4,467,802 A | 8/1984 | Maslanka |
| 4,512,345 A | 4/1985 | Green |
| 4,569,131 A | 2/1986 | Falk et al. |
| 4,733,664 A | 3/1988 | Kirsch et al. |
| 4,763,668 A | 8/1988 | Macek et al. |
| 4,765,335 A | 8/1988 | Schmidt et al. |
| 4,805,618 A | 2/1989 | Ueda et al. |
| 4,950,273 A | 8/1990 | Briggs |
| 5,029,355 A | 7/1991 | Thai |
| 5,100,418 A | 3/1992 | Yoon et al. |
| 5,141,519 A | 8/1992 | Smith et al. |
| 5,152,778 A | 10/1992 | Bales, Jr. et al. |
| 5,174,276 A | 12/1992 | Crockard |
| 5,192,298 A | 3/1993 | Smith et al. |
| 5,201,743 A | 4/1993 | Haber et al. |
| 5,209,747 A | 5/1993 | Knoepfler |
| 5,275,608 A | 1/1994 | Forman et al. |
| 5,275,613 A | 1/1994 | Haber et al. |
| 5,275,615 A | 1/1994 | Rose |
| 5,282,806 A | 2/1994 | Haber et al. |
| 5,318,589 A | 6/1994 | Lichtman |
| 5,368,606 A | 11/1994 | Marlow et al. |
| 5,471,992 A | 12/1995 | Banik et al. |
| 5,571,137 A | 11/1996 | Marlow et al. |
| 5,618,303 A | 4/1997 | Marlow et al. |
| 5,632,764 A | 5/1997 | Beideman et al. |
| 5,702,407 A | 12/1997 | Kaji |
| 5,766,184 A | 6/1998 | Matsuno et al. |
| 5,766,189 A | 6/1998 | Matsuno |
| 5,792,165 A | 8/1998 | Kilieman et al. |
| 5,797,923 A | 8/1998 | Aiyar et al. |
| 5,964,779 A | 10/1999 | Mayenberger et al. |
| 6,059,719 A | 5/2000 | Yamamoto et al. |
| 6,358,197 B1 | 3/2002 | Silverman et al. |
| 6,814,742 B2 | 11/2004 | Kimura et al. |
| 6,923,818 B2 | 8/2005 | Muramatsu et al. |
| 7,011,667 B2 | 3/2006 | Kobayashi et al. |
| 7,041,118 B2 | 5/2006 | Muramatsu et al. |
| 7,081,121 B2 | 7/2006 | Muramatsu et al. |
| 7,223,271 B2 | 5/2007 | Muramatsu et al. |
| 7,223,272 B2 | 5/2007 | Francese et al. |
| 7,326,221 B2 | 2/2008 | Sakamoto |
| 7,452,327 B2 | 11/2008 | Durgin et al. |
| 7,488,334 B2 | 2/2009 | Jugenheimer et al. |
| 7,494,461 B2 | 2/2009 | Wells et al. |
| 7,601,159 B2 | 10/2009 | Ewers et al. |
| 7,722,628 B2 | 5/2010 | Stokes et al. |
| 7,727,247 B2 | 6/2010 | Kimura et al. |
| 7,736,372 B2 | 6/2010 | Reydel et al. |
| 7,736,374 B2 | 6/2010 | Vaughan et al. |
| 7,740,639 B2 | 6/2010 | Hummel et al. |
| 7,744,613 B2 | 6/2010 | Ewers et al. |
| 7,766,810 B2 | 8/2010 | Ohdaira |
| 7,776,057 B2 | 8/2010 | Laufer et al. |
| 7,815,652 B2 | 10/2010 | Messerly et al. |
| 8,083,668 B2 | 12/2011 | Durgin et al. |
| 8,088,061 B2 | 1/2012 | Wells et al. |
| 2002/0151916 A1 | 10/2002 | Muramatsu et al. |
| 2002/0173805 A1 | 11/2002 | Matsuno et al. |
| 2002/0177861 A1 | 11/2002 | Sugiyama et al. |
| 2003/0069592 A1 | 4/2003 | Adams et al. |
| 2003/0097146 A1 | 5/2003 | Montalvo et al. |
| 2004/0044363 A1 | 3/2004 | Fowler |
| 2005/0059985 A1 | 3/2005 | Kimura |
| 2005/0101991 A1 | 5/2005 | Ahlberg et al. |
| 2005/0234296 A1 | 10/2005 | Saadat et al. |
| 2005/0251183 A1 | 11/2005 | Buckman et al. |
| 2005/0272977 A1 | 12/2005 | Saadat et al. |
| 2006/0084886 A1 | 4/2006 | Reydel |
| 2006/0155308 A1 | 7/2006 | Griego |
| 2006/0258905 A1 | 11/2006 | Kaji et al. |
| 2006/0259045 A1 | 11/2006 | Damarati |
| 2007/0073185 A1 | 3/2007 | Nakao |
| 2007/0135678 A1 | 6/2007 | Suzuki |
| 2007/0239162 A1 | 10/2007 | Bhatnagar et al. |
| 2007/0250113 A1 | 10/2007 | Hegeman et al. |
| 2007/0287993 A1 | 12/2007 | Hinman et al. |
| 2008/0004656 A1 | 1/2008 | Livneh |
| 2008/0147113 A1 | 6/2008 | Nobis et al. |
| 2008/0171907 A1 | 7/2008 | Long et al. |
| 2008/0228199 A1 | 9/2008 | Cropper et al. |
| 2008/0228202 A1 | 9/2008 | Cropper et al. |
| 2008/0234703 A1 | 9/2008 | Cropper et al. |
| 2008/0234705 A1 | 9/2008 | Cropper et al. |
| 2008/0255427 A1 | 10/2008 | Satake et al. |
| 2008/0262539 A1 | 10/2008 | Ewers et al. |
| 2008/0269557 A1 | 10/2008 | Marescaux et al. |
| 2008/0269566 A1 | 10/2008 | Measamer |
| 2008/0275441 A1 | 11/2008 | Aue |
| 2008/0287963 A1 | 11/2008 | Rogers et al. |
| 2008/0294178 A1 | 11/2008 | Kortenbach et al. |
| 2008/0300461 A1 | 12/2008 | Shaw et al. |
| 2008/0300624 A1 | 12/2008 | Schwemberger et al. |
| 2009/0005638 A1 | 1/2009 | Zwolinski |
| 2009/0018602 A1 | 1/2009 | Mitelberg et al. |
| 2009/0043316 A1 | 2/2009 | Durgin et al. |
| 2009/0062792 A1 | 3/2009 | Vakharia et al. |
| 2009/0138006 A1 | 5/2009 | Bales et al. |
| 2009/0138028 A1 | 5/2009 | Wells et al. |
| 2009/0143794 A1 | 6/2009 | Conlon et al. |
| 2009/0163934 A1 | 6/2009 | Raschdorf, Jr. et al. |
| 2009/0192344 A1 | 7/2009 | Bakos et al. |
| 2009/0221915 A1 | 9/2009 | Voegele et al. |
| 2009/0299385 A1 | 12/2009 | Stefanchik et al. |
| 2009/0306683 A1 | 12/2009 | Zwolinski et al. |
| 2009/0306686 A1 | 12/2009 | Ohdaira |
| 2009/0326518 A1 | 12/2009 | Rabin |
| 2009/0326578 A1 | 12/2009 | Ewers et al. |
| 2010/0042115 A1 | 2/2010 | Saadar et al. |
| 2010/0057078 A1 | 3/2010 | Arts et al. |
| 2010/0057085 A1 | 3/2010 | Holcomb et al. |
| 2010/0130817 A1 | 5/2010 | Conlon |
| 2010/0168787 A1 | 7/2010 | Surti |
| 2010/0179540 A1 | 7/2010 | Marczyk et al. |
| 2010/0198149 A1 | 8/2010 | Fox |
| 2010/0198248 A1 | 8/2010 | Vakharia |
| 2010/0211086 A1 | 8/2010 | Ewers et al. |
| 2010/0217151 A1 | 8/2010 | Gostout et al. |
| 2010/0217292 A1 | 8/2010 | Kimura et al. |
| 2010/0217293 A1 | 8/2010 | Kimura et al. |
| 2010/0217294 A1 | 8/2010 | Kimura et al. |
| 2010/0249498 A1 | 9/2010 | Wingardner et al. |
| 2010/0249700 A1 | 9/2010 | Spivey |
| 2010/0249808 A1 | 9/2010 | Harada et al. |
| 2012/0016391 A1 | 1/2012 | Aguirre |
| 2012/0089158 A1 | 4/2012 | Martinez et al. |
| 2012/0109160 A1 | 5/2012 | Martinez et al. |
| 2012/0165863 A1 | 6/2012 | McLawhorn |

FOREIGN PATENT DOCUMENTS

| | | |
|---|---|---|
| DE | 19906360 A1 | 8/2000 |
| DE | 102006003548 | 8/2007 |
| JP | 57-156752 | 9/1982 |
| JP | 60-103946 | 6/1985 |
| JP | 63-6016 | 2/1988 |
| JP | 63-267345 | 11/1988 |
| JP | 63-288147 | 11/1988 |
| JP | 2-6011 | 1/1990 |
| JP | 2007950 | 1/1990 |
| JP | 4-26091 | 3/1992 |
| JP | 4102450 | 4/1992 |
| JP | 5-212043 | 8/1993 |
| JP | 5208020 | 8/1993 |
| JP | 5212042 | 8/1993 |
| JP | 6237939 | 8/1994 |
| JP | 6254101 | 9/1994 |
| JP | 8019548 | 1/1996 |
| JP | 8126648 | 5/1996 |
| JP | 8280701 | 10/1996 |
| JP | 8308847 | 11/1996 |
| JP | 9038093 | 2/1997 |
| JP | 9289989 | 11/1997 |

(56) References Cited

FOREIGN PATENT DOCUMENTS

| JP | 2000-33090 | 2/2000 |
|---|---|---|
| JP | 2000-335631 | 12/2000 |
| JP | 2001-520069 | 10/2001 |
| JP | 2002-224124 | 8/2002 |
| JP | 2002-301082 | 10/2002 |
| JP | 2002-360585 | 12/2002 |
| WO | WO 9614020 | 5/1996 |
| WO | WO 99/20183 | 4/1999 |
| WO | WO 2004/017839 | 4/2004 |
| WO | WO 2008/005433 | 1/2008 |
| WO | WO 2010/078163 | 7/2010 |
| WO | WO 2011/087723 | 7/2011 |
| WO | WO 2012/051188 | 4/2012 |
| WO | WO 2012/051191 | 4/2012 |
| WO | WO 2012/051200 | 4/2012 |
| WO | WO 2012/083041 | 6/2012 |
| WO | 2012/051200 | 11/2012 |

OTHER PUBLICATIONS

Cooper Surgical brochure on the Marlow Nu-Tip Laparoscopic Instruments (2006).
Medicon Instrument Catalog, pp. 440, 441, 443, 451, 585, 686 (1986).
V. Mueller, The Surgical Armamentarium, pp. F176-F177 (1988).
Annex to Form PCT/ISA/206—Communication Relating to the Results of Partial International Search for PCT/US2011/055800 (Jun. 28, 2012).
International Search Report/Written Opinion for PCT/US2009/069270 (May 17, 2010).
International Search Report/Written Opinion for PCT/US2010/061077 (Apr 1, 2011).
International Search Report and Opinion for PCT/US2011/055780 (Jun. 14, 2012).
International Search Report and Opinion for PCT/US2011/055786 (Jun. 19, 2012).
International Search Report and Opinion for PCT/US2011/065200 (Jun. 13, 2012).
International Search Report and Opinion for PCT/US2011/055800 (Sep. 12, 2012).
International Search Report and Opinion for PCT/US2012/046666 (Oct. 8, 2012).
Office Action dated Jan. 18, 2012 for U.S. Appl. No. 12/645,004 in related application.
Office Action dated May 29, 2012 for U.S. Appl. No. 12/645,004 in related application.
Office Action dated Dec. 20, 2012 for U.S. Appl. No. 13/186,427 in related application.

MEDICAL DEVICES WITH DETACHABLE PIVOTABLE JAWS

CROSS-REFERENCE TO RELATED APPLICATIONS

This application is a Continuation-In-Part of U.S. patent application Ser. No. 12/971,873 filed on Dec. 17, 2010, and also claims the benefit of U.S. Provisional Patent Application Ser. No. 61/391,875 filed on Oct. 11, 2010. All of the foregoing applications are hereby incorporated by reference.

BACKGROUND

Conventionally, a clip may be introduced into a body cavity through an endoscope to grasp living tissue of a body cavity for hemostasis, marking, and/or ligating. Such clips are often known as surgical clips, endoscopic clips, hemostasis clips and vascular clips. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding. Clips have also been attempted for use in closing perforations in the stomach Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices such as clips have been used in various parts of the body, including gastrointestinal applications. One of the problems associated with conventional hemostatic devices and clips, however, is that many devices are not strong enough to cause permanent hemostasis. Further, clips have also been attempted for use in closing perforations in the stomach or gastrointestinal structures, but unfortunately traditional clips suffer from difficult placement and the capability to grasp a limited amount of tissue, potentially resulting in incomplete closure.

SUMMARY

The invention may include any of the following aspects in various combinations and may also include any other aspect described below in the written description or in the attached drawings.

In a first aspect, a medical device is provided for engaging tissue, the medical device including a housing, first and second jaws, first and second links, and a driver. The housing defines an internal passageway and a longitudinal axis extending between proximal and distal ends of the housing. The housing also defines a jaw guide surface, a first link guide surface and a second link guide surface, each of the guide surfaces extending longitudinally between proximal and distal ends of the guide surfaces. The first jaw is slidably and pivotally connected to the housing, and has proximal and distal ends. The first jaw is slidably received within the internal passageway for longitudinal movement along the jaw guide surface. The second jaw is slidably and pivotally connected to the housing, and has proximal and distal ends. The second jaw is slidably received within the internal passageway for longitudinal movement along the jaw guide surface. The first link has first and second ends. The first end is pivotally attached to the first jaw, and the second end is slidably and pivotally attached to the housing for longitudinal movement along the first link guide surface. The second link has first and second ends. The first end is pivotally attached to the second jaw, and the second end is slidably and pivotally attached to the housing for longitudinal movement along the second link guide surface. The driver is operatively connected to the first and second jaws, whereby longitudinal movement of the driver moves the first and second jaws longitudinally along the jaw guide surface and moves the second ends of the first and second links along the first and second link guide surfaces. Longitudinal movement of the driver rotates the first and second jaws relative to the housing when the second ends of the first and second links reach the distal ends of the first and second link guide surfaces.

According to more detailed aspects, the proximal ends of the first and second jaws are slidably and pivotally attached to the housing. Preferably, the proximal ends are pivotally attached to the housing about a shared jaw pivot axis. A jaw pivot pin may be used to pivotally connect the proximal ends of both the first and second jaws to the housing. The jaw guide surface is defined by opposing jaw slots formed in the housing, the opposing jaw slots receiving opposing ends of the jaw pivot pin. Preferably, the jaw guide surface extends longitudinally and parallel to the central axis. The jaw guide surface may be located between the first and second link guide surfaces. The first ends of the first and second links are pivotally attached at a midpoint of the first and second jaws, respectively, while the second ends of the first and second links are slidably and pivotally connected to the housing.

According to further detailed aspects, the driver is engaged with the proximal ends of the first and second jaws when the driver is moved distally. The driver is engaged with the second ends of the first and second links when the driver is moved proximally. Preferably, the driver includes a distal end for engaging the first and second jaws, the distal end of the driver including a first flange which engages the proximal end of the first jaw and is shaped to permit rotation of the first jaw relative to the first flange while engaged, the distal end of the driver including a second flange which engages the proximal end of the second jaw and is shaped to permit rotation of the second jaw relative to the second flange while engaged. The driver extends longitudinally to a position located proximal to the second ends of the first and second links.

According to still further detailed aspects, the first and second jaws are longitudinally slidable between an extended position and a retracted position, and the housing is structured to block rotation of the first and second jaws when in their retracted positions, and the housing is structured to permit rotation of the first and second jaws when in their extended positions. The first and second links are also longitudinally slidable between an extended position and a retracted position, and at the same time or alternatively, the housing is structured to block rotation of the first and second links when in their retracted positions, and the housing is structured to permit rotation of the first and second links when in their extended positions. The housing, the first link, and the first jaw are pivotable relative to each other, and the housing, the second link, and the second jaw are pivotable relative to each other, and further the second ends of the first and second links are longitudinally slidable relative to the proximal ends of the first and second jaws, whereby the distance between the second ends and proximal ends determines the rotation of the first and second jaws between a closed configuration and an open configuration. The device may also include an elongate drive wire selectively connected to the driver for longitudinal movement therewith, and an elongate tubular member (e.g. a catheter) selectively connected to the housing. Sufficient proximal translation of the drive wire disconnects the driver from the drive wire and the housing from the elongate tubular member.

According to more detailed aspects, the device may also include a first link pivot pin that pivotally connects the second end of the first link to the housing, and a second link pivot pin that pivotally connects the second end of the second link to the housing. The first link guide surface is defined by opposing first link slots formed in the housing, and the second link guide surface is defined by opposing second link slots formed in the housing, wherein the opposing first link slots receive opposing ends of the first link pivot pin, and wherein the opposing second link slots receive opposing ends of the second link pivot pin.

In a second aspect, a method is provided for clamping tissue. The method includes providing a medical device comprising a housing, first and second jaws, first and second links, and a driver, wherein the first and second jaws are slidably and pivotally connected to the housing, the first and second links are slidably and pivotally connected to the housing, the first and second links are pivotally attached to the first and second jaws, respectively, and the driver is operatively connected to the first and second jaws. The driver is advanced distally to translate the first and second jaws and the first and second links distally relative to the housing. The distal translation of the first and second links is limited or blocked while further advancing the driver distally to rotate the first and second jaws relative to the housing. The driver is retracted proximally to rotate the first and second jaws relative to the housing. According to more detailed aspects, the medical device may further comprise an elongated drive wire selectively connected to the driver for longitudinal movement therewith, and the drive wire may be detached from the driver.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

An exemplary medical system 20 having a medical device 40 for engaging tissue T (FIG. 11) is shown in FIGS. 1 through 4. The medical system 20 and device 40 are generally sized and structured for operation through the working channel of an endoscope (not shown) or other scope, although the system 20 and device 40 may also be used alone or in conjunction with other elongate devices such as catheters, fiber-optic visualization systems, needles and the like. Generally, the medical system 20 includes a drive wire 22 slidably housed within the distal end 23 of a catheter 24 for selective connection to, and operation of, the medical device 40. As will be described in further detail herein, the medical device 40 generally includes a housing 42 having a first jaw 44 and a second jaw 46 pivotally connected thereto for engaging the tissue T. Generally, the jaws 44, 46 have been shown as forming grasping forceps, although the jaws are intended to be used to clip tissue, e.g. to close an opening or for hemostasis. Accordingly, it will be recognized that the shape and structure of the jaws may take many forms and serve many purposes and functions, all in accordance with the teachings of the present invention.

In the medical system 20, the drive wire 22 slidably extends through the catheter 24. Although the term "wire" is used to refer to the drive wire 22, it will be recognized that any elongate control member capable of transmitting longitudinal force over a distance (such as is required in typical endoscopic, laparoscopic and similar procedures) may be used, and this includes plastic rods or tubes, single filament or multi-filament wires and the like. The drive wire 22 should also be capable of properly transmitting a rotational/torsional force from the proximal end to the distal end to rotate the medical device 40 and jaws 44, 46, and thus it is currently preferred that the drive wire 22 is formed from nitinol (e.g. a nitinol wire) or other superelastic alloy.

A connection block 26 is slidably fitted within the distal end 23 of the catheter 24 and defines a bore 28 therethrough which slidably receives the drive wire 22. The exterior of the connection block 26 includes a recessed portion 27, and two pins 30 (e.g., formed from stainless steel wire) are connected to the catheter 24 and positioned within the recessed portion 27 (i.e. between proximal and distal flanges defining the recessed portion 27) to limit the longitudinal movement of the connection block 26.

A distal end of the drive wire 22 defines a distal head 32 that is sized larger than the drive wire 22, and likewise larger than the bore 28 in the connection block 26. As will be described later herein, the distal head 32 is used to slide the connection block 26 within the catheter 24 to disconnect the medical device 40 from the medical system 20. As also seen in FIGS. 1-4, the housing 42 of the medical device 40 is a tubular member defining an interior space 43. A proximal end of the housing 42 frictionally receives a distal end of the connection block 26 within the interior space 43 for selective connection therewith.

Figures 5, 6:
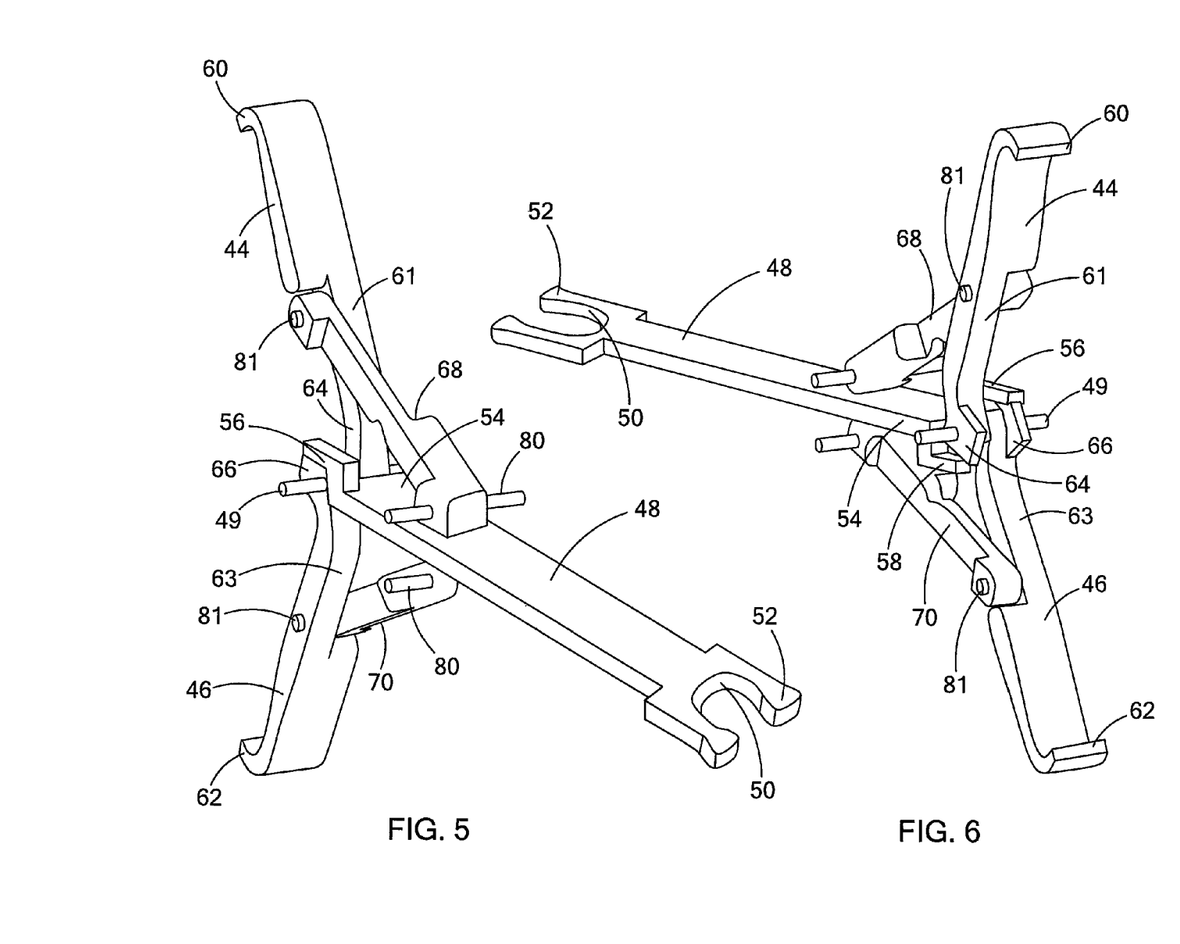
FIG. 5 is a front perspective view of interior structures of the medical system and device depicted in FIGS. 1-4.
FIG. 6 is a rear perspective view of interior structures of the medical system and device depicted in FIGS. 1-4.

The internal passageway 43 of the housing 42 also receives the first and second jaws 44, 46 and a driver 48 which is used to interconnect the drive wire 22 to the jaws 44, 46. As best seen in FIG. 5, the first and second jaws 44, 46 include distal ends 60, 62 that are structured to grasp and engage tissue, which have a talon shape as disclosed in 61/141,934 filed Dec. 31, 2008, the disclosure of which is incorporated herein by reference in its entirety. Generally, distal translation of the driver 48 causes the first and second jaws 44, 46 to rotate outwardly away from each other, while proximal retraction of the driver 48 causes the first and second jaws 44, 46 to rotate inwardly toward one another.

As best seen in FIGS. 1, 2 and 5-6, the driver 48 has a proximal portion which defines a socket 50 sized to receive enlarged distal head 32 of the drive wire 22. At the proximal entrance of the socket 50, two deflectable locking tabs 52 are formed which rotate relative to the remainder of the driver 48 to increase or decrease the size of the socket 50. The locking tabs 52 may be separately formed and pivotally attached to the driver 48, or may be integrally formed with the driver 48 and formed of a resilient material which flexes to permit rotation of the locking tabs 52 radially inwardly and radially outwardly. Preferably the locking tabs 52 are plastically deformable, such that they may be locked to the drive wire 22 or to the housing 42, as discussed further herein.

As best seen in FIGS. 5-6, a distal portion of the driver 48 defines a two L-shaped flanges 56, 58 for engaging and operating the jaws 44, 46. The inner surface of flange 56 engages a proximal end 66 of jaw 46, while the inner surface of flange 58 engages a proximal end 64 of jaw 44. The flanges 56, 58 are shaped to permit rotation of the proximal ends 64, 66 of the jaws 44, 46 relative to the flanges 56, 58 while engaged therewith. While the flanges 56, 58 and proximal ends 64, 66 have been shown as squared-off (so that they firmly engage in the fully open, and fully closed, positions), the mating surfaces may be rounded or otherwise shaped to promote rotation between the flanges 56, 58 and the proximal ends 64, 66 of the jaws 44, 46.

Figure 3:
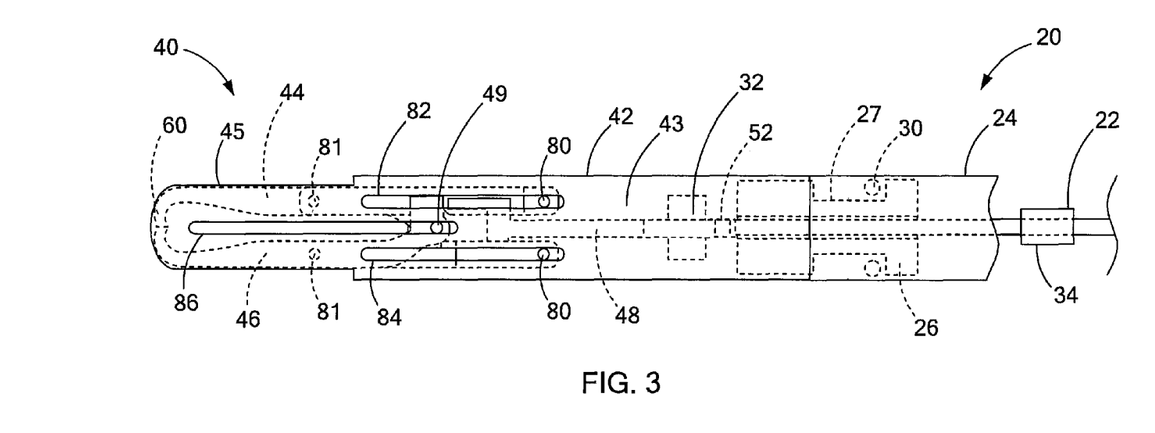
FIG. 3 is a side view of the medical system and device depicted in FIG. 1.
Figure 4:
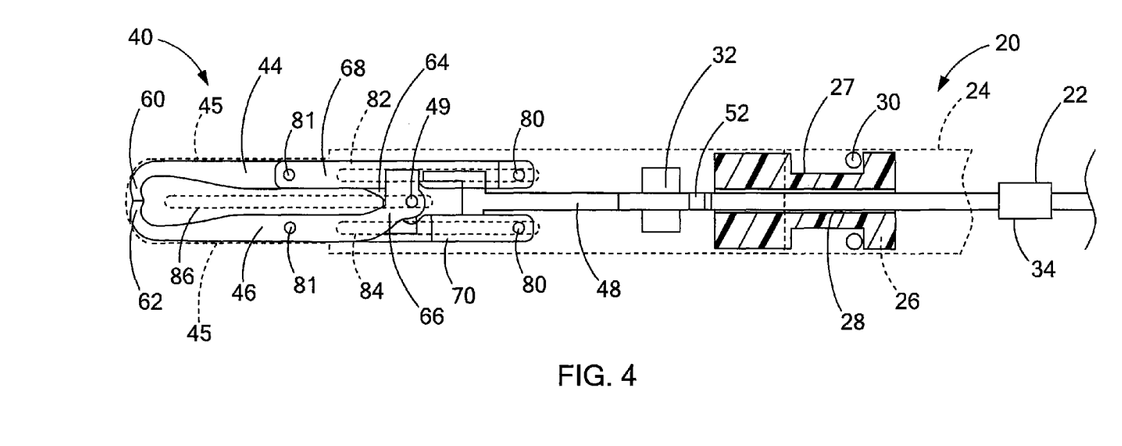
FIG. 4 is a side view similar to FIG. 3, but showing the outer structures in dotted lines and the interior structures in solid lines and partial cross section

The proximal ends 64, 66 of jaws 44, 46 are pivotally attached to the housing 42 directly via a pin 49 which extends through the proximal ends 64, 66 and through opposing jaw slots 86 formed in the housing, as best seen in FIGS. 3-4. By virtue of the jaw slots 86, the jaws 44, 46 are thus both pivotally, and slidably, attached to the housing 42. The opposing jaw slots 86 thus act and define a jaw guide surface of the housing 42 which guides longitudinal movement of the jaws 44, 46 relative to the housing. The distal ends of the jaw slots 86 also serve to restrict the longitudinal movement of the jaws 44, 46 relative to the housing 42. It will be recognized that the jaw guide surface could also be formed by channels, recesses or other structures formed into the housing 42, instead of, or in conjunction with, the jaw slots 86. During assembly, the slots allow the pins of the device 40 to be inserted after the jaws, links and driver are positioned with the housing, and the slots may later be covered with a sleeve, strip, secondary housing or other material if desired.

Figure 1:
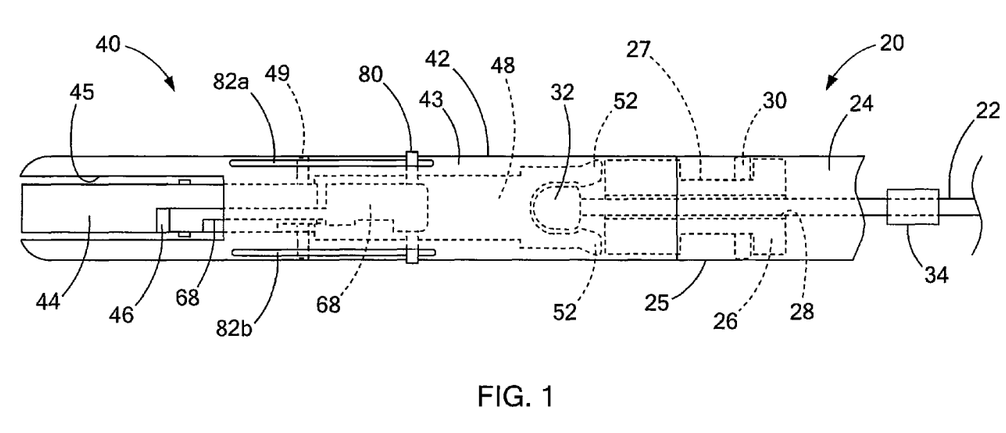
FIG. 1 is a top view of a medical system having a medical device for engaging tissue, constructed in accordance with the teachings of the present invention.
Figure 2:
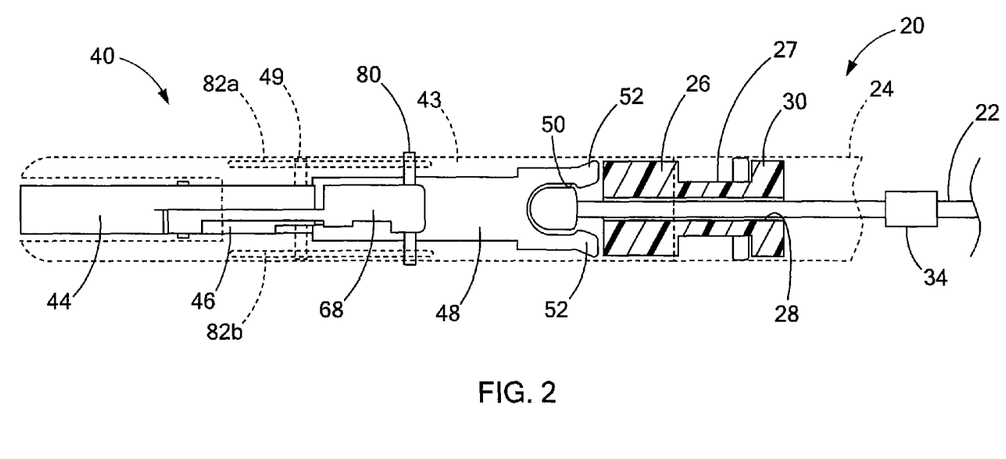
FIG. 2 is a top view similar to FIG. 1, but showing the outer structures in dotted lines and the interior sections in solid lines and partial cross-section.

Turning back to FIGS. 5 and 6, the first and second jaws 44, 46 are also indirectly connected to the housing 42 via first and second links 68, 70, respectively. Distal ends of the first and second links 68, 70 are pivotally attached to first and second jaws 44, 46 via pivots 81. The pivotal connections (pivots 81) are formed at a midpoint of the first and second jaws 44, 46, i.e. anywhere between the proximal ends 66, 68 and the distal ends 60, 62 of the first and second jaws 44, 46. The proximal ends of the first and second links 68, 70 are slidably and pivotally attached to the housing 42 via two pins 80. In particular, and as best seen in FIGS. 3-4, the housing 42 defines opposing first link slots 82 that are sized and positioned to receive the pin 80 of the first link 68, as well as opposing second link slots 84 that are sized and positions to receive the pin 80 of the second link 70. In FIGS. 1-2, the opposing first link slots 82 are individually identified by reference numerals 82a and 82b. Accordingly, the opposing first and second link slots 82, 84 act and define first and second link guide surfaces of the housing 42 which guide longitudinal movement of the first and second links 68, 70 relative to the housing 42. As with the jaw guide surface, the first and second link guide surfaces could also be formed by channels, recesses or other structures formed into the housing 42, instead of, or in conjunction with, the first and second link slots 82, 84.

The driver 48 extends between the proximal ends of the first and second links 68, 70, and engages the proximal ends 64, 66 of the first and second jaws 44, 46 to first expose and then open the jaws 44, 46, as shown in FIGS. 5 and 6. At the same time, the proximal ends of the links 68, 70 and their pins 80 are located such that proximal retraction of the driver 48 (via drive wire 22) causes the outer surface of the L-shaped flanges 56, 58 to engage the pins 80 (or links 68, 70) for retraction and closing of the jaws 44, 46, as will be described in further detail below. It can thus be seen that the jaw guide surface of slot 86 is located between the first and second link guide surfaces of slots 82, 84 (which are above and below the slot 86), as best seen in FIGS. 3-4.

The internal passageway 43 of the housing 42 extends through the distal end of the housing 42, and it is through this passageway 43 that the first and second jaws 44, 46 can extend. Additionally, as shown in FIGS. 1-4, the housing 42 defines opposing slots 45 which are sized to permit the first and second jaws 44, 46 and the first and second links 68, 70 to pass therethrough when they rotate radially outwardly. Accordingly, it is also clear from FIGS. 1 and 2 that the housing 42 serves to block rotation of the first and second links 68, 70 when they are entirely or partially contained within the internal passageway 43 of the housing 42. Suitable plastics for forming the housing include, but are not limited to, polytetrafluorethylene (PTFE), expanded polytetrafluorethylene (EPTFE), polyethylene ether keytone (PEEK), polyvinylchloride (PVC), polycarbonate (PC), polyamide, polyimide, polyurethane, polyethylene (high, medium or low density), and suitable metals include stainless steel, nitinol and similar medical grade metals and alloys.

Figure 7:
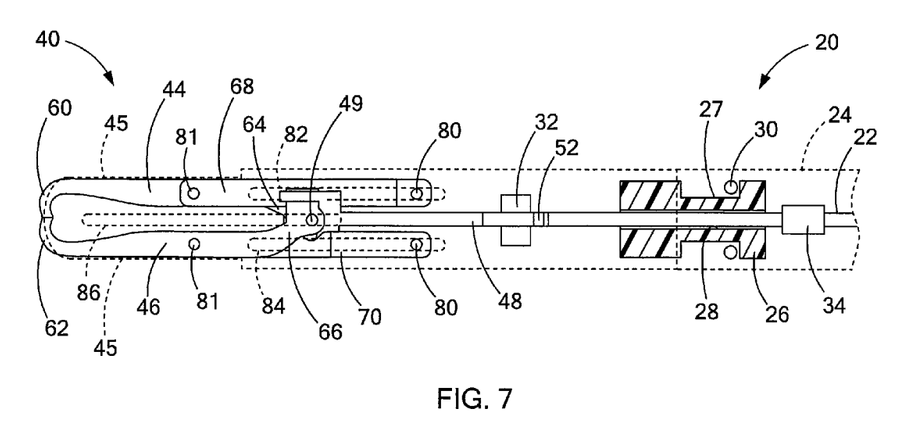
FIGS. 7-11 are side views showing operation of the medical system and device depicted in FIGS. 1-4.
Figure 8:
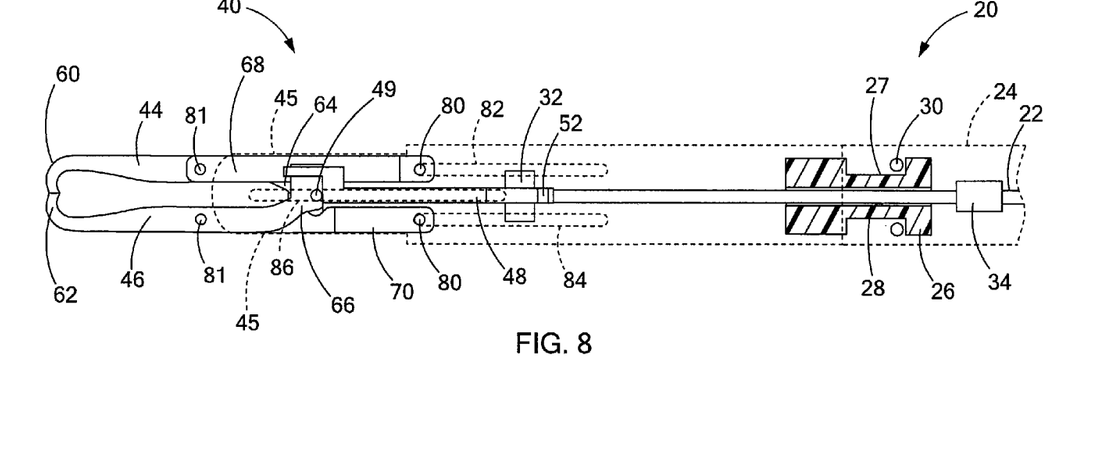

Turning to the sequence of FIGS. 7-11, operation of the medical device 40 will now be described. As shown in FIG. 7, the first and second jaws 44, 46 are shown in a retracted position where they are substantially contained within the housing 42. Depending on the application, the distal ends 60, 62 of the jaws 44, 46 may slightly project from the distal end of the housing 42 in their retracted positions, or they may be entirely positioned within the housing 42. When the drive wire 22 is translated distally (to the left on the page in FIG. 7) the distal head 32 engages the driver 48, which in turn engages the proximal ends 64, 66 of the jaws 44, 46 (via the driver's flanges 56, 58 (FIGS. 5-6)), causing the jaws 44, 46 to slide distally through and out of the housing 42, as shown in FIG. 8. As previously mentioned, this longitudinal movement is guided by the jaw guide surface of jaw slot 86 (receiving pin 49), and the link guide surfaces of link slots 82, 84 (receiving pins 80) which slidably and pivotally connect the jaws 44, 46 to the housing 42.

Figure 9:
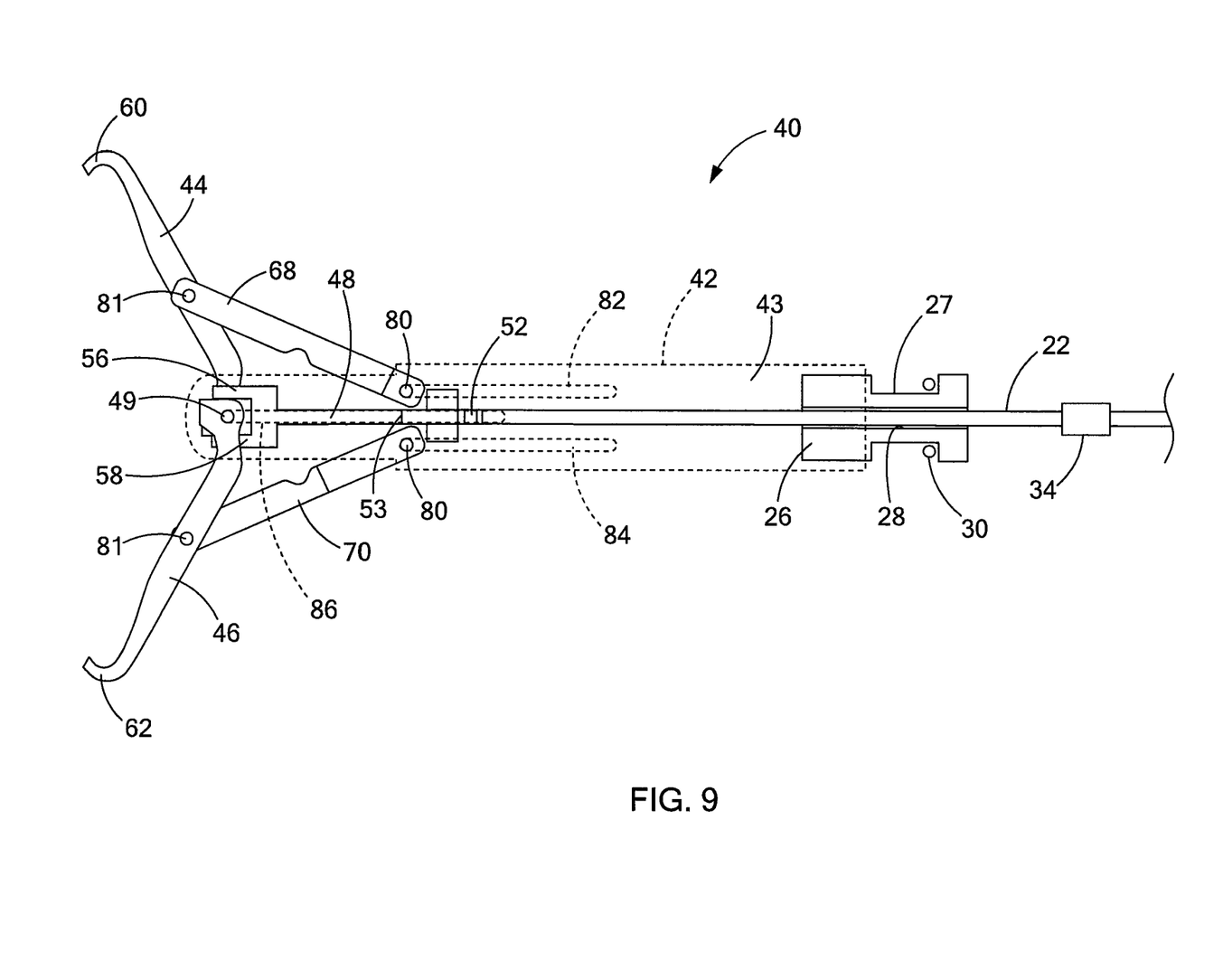

As shown in FIG. 8, the first and second jaws 44, 46 have an extended position where the jaws substantially project from a distal end of the housing 42. In this extended position, the pins 80 at the proximal ends of the first and second links 68, 70 have reached the end of their slots 82, 84, while the pin 49 at the proximal ends 64, 66 of the jaws 44, 46 have not reached the end of slot 86. Accordingly, it will be seen that further distal advancement of drive wire 22, and hence the driver 48, causes the proximal ends 64, 66 of jaws 44, 46 to continue moving distally (to the left on the page), while the links 68, 70 induce rotation of the jaws 44, 46 away from each other, as shown in FIG. 9. Eventually, the pin 49 reaches the end of jaw slot 86, at which point the jaws 44, 46 are fully open. The jaws 44, 46 have been shown rotating about 75°, thus forming a 150° opening between them, however the housing 42 and its slots may be sized to permit rotation through a full 90° or more, thus forming at least a 180° between them. The slots 45 in the housing 42 are sized to permit the rotation of the jaws 44, 46 and links 68, 70 out of the housing, and these slots 45 may also be used to limit the rotation thereof, in addition to or separately from the sizing of the slots 82, 84, 86. It will therefore be seen that the distance between the pins 80 (at the ends of the first and second links 68, 70) and the proximal ends 64, 66 of the jaws 44, 46 determines the rotation of the first and second jaws between a closed configuration and an open configuration.

Figure 10:
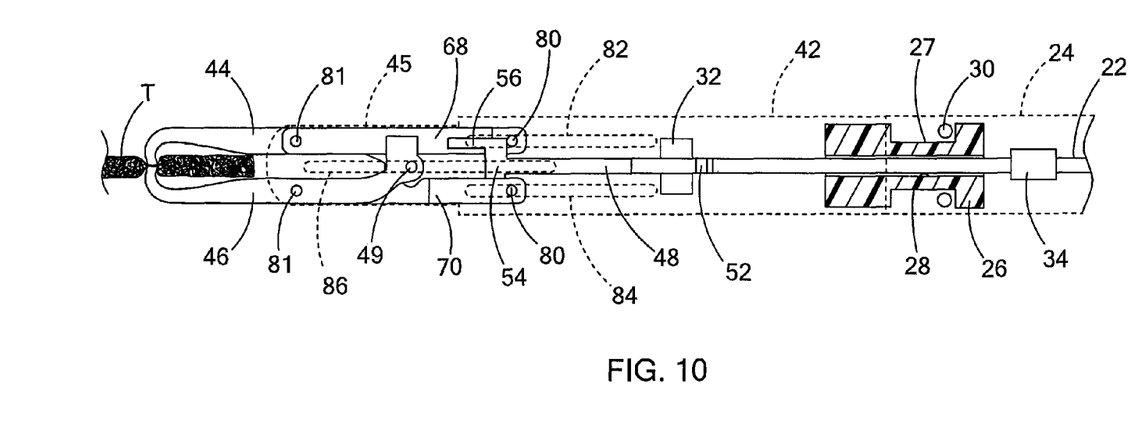
Figure 11:
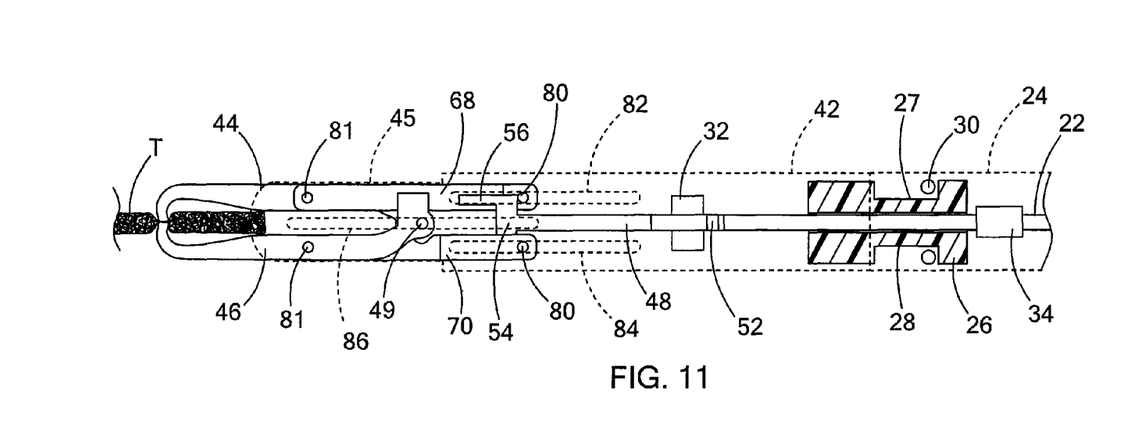

In the tissue receiving configuration (open configuration) shown in FIG. 9, the medical device 40 and its jaws 44, 46 may be positioned adjacent tissue T. As shown in FIG. 10, the tissue T may be placed between the first and second jaws 44, 46 and the jaws 44, 46 rotated back towards their position shown in FIG. 8. The tissue T has been shown as a single layer, although multiple layers may be clipped between the jaws 44, 46. Generally, proximal retraction of the drive wire 22 and the driver 48 causes the flanges 56, 58 of the driver 48 to engage the pins 80 at the proximal ends of the links 68, 70. In particular, as also clear from FIGS. 5 and 6, the flange 56 will engage pin 80 of the first link 68, and flange 58 will engage pin 80 of second link 70. As the links 68, 70 are pulled proximally (to the right on the page) the housing 42 presses on the links 68, 70 (and/or the jaws 44, 46) and causes them to rotate towards each other to grasp the tissue T therebetween. Depending on their orientation relative to the patient and the ground, the jaws 44, 46 may also naturally collapse towards each other. As shown in FIG. 11, further proximal retraction of the drive wire 22 and driver 48 will cause the jaws 44, 46 to move longitudinally in a proximal direction (to the right on the page in FIG. 11).

Figure 12:
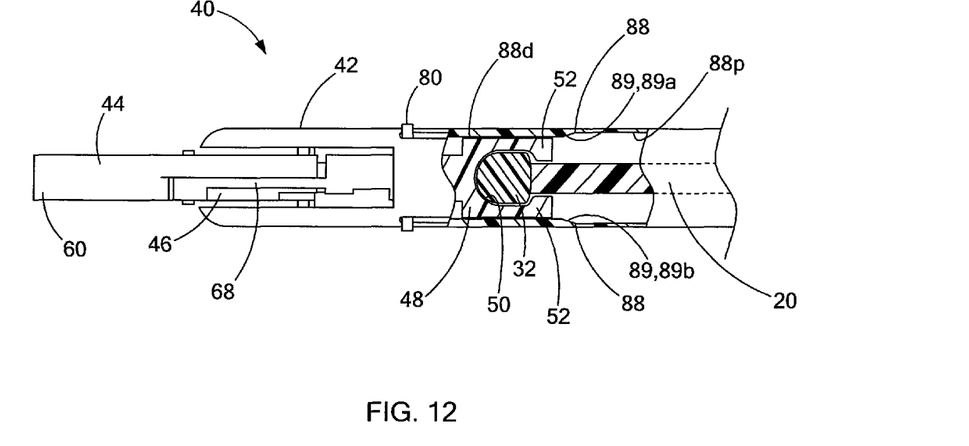
FIGS. 12 and 13 are top views, partially in cross-section, depicting operation of the medical system and device depicted in FIGS. 1-4.

In order for the medical device 40 to serve as a clip and maintain its grasp on the tissue T, or to maintain the clipping of two layers of tissue against each other, the jaws 44, 46 may be locked in position and the drive wire 22 of the medical system 20 disconnected from the medical device 40. As shown in FIG. 12, the interior of the housing 42 also defines a driver guide surface 88 (which guides the driver 48) that has a proximal portion 88p and a distal portion 88d. The proximal portion 88p of the driver guide surface 88 has a width (measured up and down on the page in FIG. 12) that is greater than a width of the distal portion 88d of the driver guide surface 88. The driver guide surface 88 may be formed by opposing surfaces or C-shaped channels in the housing 42. The transition between the proximal portion 88p and distal portion 88d defines a shoulder 89, and namely two shoulders 89a, 89b on opposing sides of the housing 42. The shoulders 89a, 89b are sized and positioned to engage the locking tabs 52 located on the driver 48.

Figure 13:
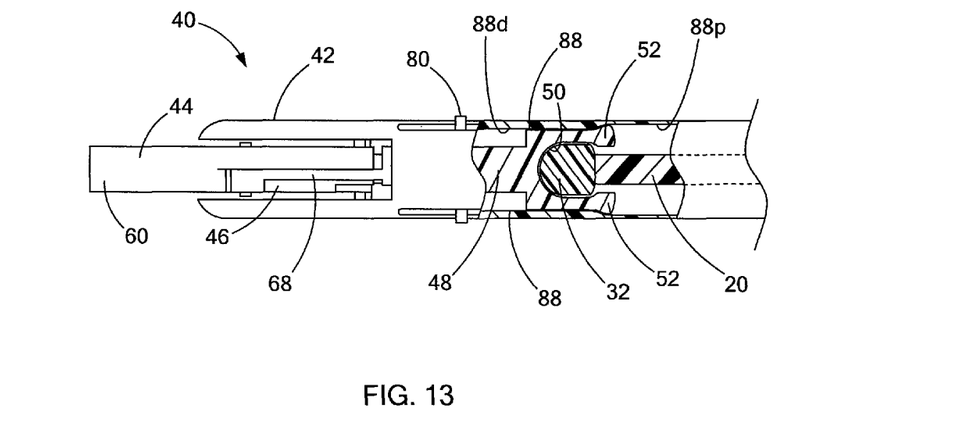

As shown in FIG. 12, when the driver 48 is located within the distal portion 86d of the third guide surface 86, the locking tabs 52 are forced radially inwardly into firm frictional engagement with the enlarged head 32 and/or the drive wire 22. Stated another way, the socket 50 formed by the driver 48 that receives the distal head 32 has an entrance which is narrowed by the inward deflection of the locking tabs 52. In this state depicted in FIG. 12, the drive wire 22 is firmly engaged with the driver 48 and hence the first and second jaws 44, 46. When the drive wire 22 and driver 48 are retracted proximally, for example upon grasping tissue as shown in FIG. 11, the proximal end of the driver 48 is received within the proximal portion 88p of the third guide surface 88 which has a larger width that permits outward movement of the locking tabs 52. Accordingly, in the state depicted in FIG. 13, the locking tabs 52 may be loosely and detachably connected to the distal head 32 of the drive wire 22. As such, further proximal movement of the drive wire 22 and its distal head 32 may be used to withdraw the distal head 32 from the socket 50 of the driver 48. At the same time, the locking tabs 52 move radially outwardly and into engagement with the shoulders 89a, 89b to lock the device 40 in a state where the tissue T is clipped between the jaws 44, 46. The tabs 52 may plastically deform to this outward position to maintain the closed configuration of the jaws. In the event the natural elasticity of the tissue T tends to pull the jaws 44, 46 out from the housing towards their extended position, the locking tabs 52 will abut the shoulders 89 of the driver guide surface of the housing 42 to prevent further distal movement or rotation of the jaws 44, 46.

Figure 14:
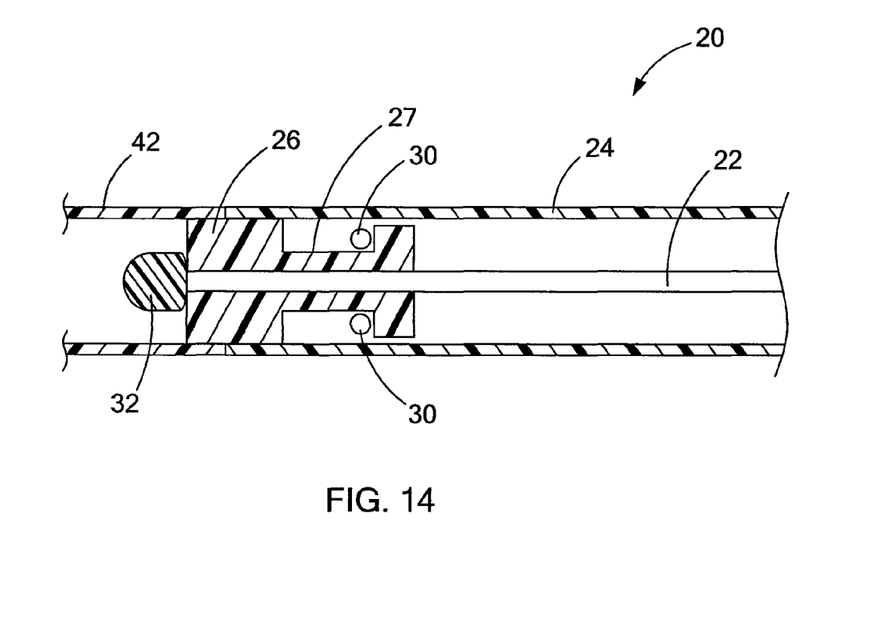
FIGS. 14 and 15 are cross-sectional views showing operation of the medical system depicted in FIGS. 1-4.
Figure 15:
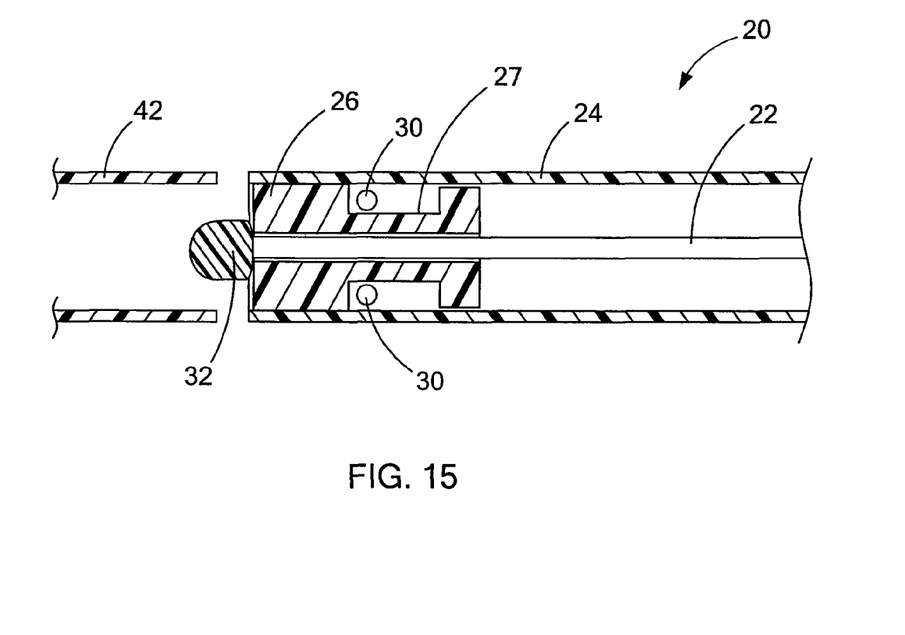

Turning now to FIGS. 14 and 15, upon still further proximal retraction of the drive wire 22 and distal head 32 (to the right on the page), the enlarged distal head 32 (or other enlarged portion of the drive wire 22) will abut the connection block 26, which is slidably fitted within the distal end 23 of the catheter 24. Sufficient proximal force on the drive wire 22 will overcome the frictional fit between the connection block 26 and the proximal end of the housing 42, thus moving the connection block 26 proximally to retract the connection block 26 within the tubular connector 24, as shown in FIG. 15. The catheter 24 can be used to provide a counterforce on the housing 42 while proximally retracting the drive wire 22 and connection block 26. Accordingly, the drive wire 22, catheter 24 and connection block 26 may be fully disconnected from the medical device 40, thereby leaving the first and second jaws 44, 46 and the housing 42 in a state having the tissue T clipped between the jaws 44, 46 and retained in vivo. The connection block 26 is retained at the distal end 23 of the catheter 24 via the pins 30, which are positioned within the recessed area 27 to engage the proximal and distal ends of the connection block 26 and limit its longitudinal movement.

The elongate catheter 24 (or other elongate tubular member such as a sheath, tube, scope or the like), which slidably encases the drive wire 22, extends proximally therealong to a proximal end of the system 20, and has a length suitable for placing the device 40 at any desire location within the body, while the proximal ends of drive wire 22 and catheter 24 are positioned outside of the body for use by the medical professional. Control handles (not shown) for controlling relative translation of the drive wire 22 and catheter 24 are well known in the art, and may be employed at the proximal end of the system 20. Additional embodiments of the connection/disconnection mechanisms and the medical system 20 may be found in copending U.S. Appl. No. 61/391,878 and Appl. No. 61/391,881, the disclosures of which are hereby incorporated by reference in their entirety.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for engaging tissue, the medical device comprising:
   a housing defining an internal passageway and a longitudinal axis extending between proximal and distal ends of the housing, the housing defining a jaw guide surface, a first link guide surface and a second link guide surface, each of the guide surfaces extending longitudinally between proximal and distal ends of their respective guide surfaces;
   a first jaw slidably and pivotally connected to the housing, the first jaw having proximal and distal ends, the first jaw slidably received within the internal passageway for longitudinal movement along the jaw guide surface;
   a second jaw slidably and pivotally connected to the housing, the second jaw having proximal and distal ends, the second jaw slidably received within the internal passageway for longitudinal movement along the jaw guide surface;
   a first link elongated in the longitudinal direction between first and second ends of the first link, the first end pivotally attached to the first jaw, the second end slidably and pivotally attached to the housing for longitudinal movement along the first link guide surface;
   a second link elongated in the longitudinal direction between first and second ends of the second link, the first end pivotally attached to the second jaw, the second end slidably and pivotally attached to the housing for longitudinal movement along the second link guide surface; and
   a driver operatively connected to the first and second jaws, longitudinal movement of the driver moving the first and second jaws longitudinally along the jaw guide surface and moving the second ends of the first and second links along the first and second link guide surfaces, longitudinal movement of the driver rotating the first and second jaws relative to the housing when the second ends of the first and second links reach the distal ends of the first and second link guide surfaces.

2. The medical device of claim 1, wherein the proximal ends of the first and second jaws are slidably and pivotally attached to the housing.

3. The medical device of claim 2, wherein the proximal ends of the first and second jaws are pivotally attached to the housing about a shared jaw pivot axis.

4. The medical device of claim 3, further comprising a jaw pivot pin that pivotally connects the proximal ends of both the first and second jaws to the housing.

5. The medical device of claim 4, wherein the jaw guide surface is defined by opposing jaw slots formed in the housing, the opposing jaw slots receiving opposing ends of the jaw pivot pin.

6. The medical device of claim 1, wherein the jaw guide surface extends longitudinally and parallel to the central axis.

7. The medical device of claim 1, wherein the jaw guide surface is located between the first and second link guide surfaces.

8. The medical device of claim 1, wherein the first ends of the first and second links are pivotally attached at a longitudinal midpoint of the first and second jaws, respectively.

9. The medical device of claim 1, wherein the second ends of the first and second links are slidably and pivotally connected to the housing.

10. The medical device of claim 1, wherein the driver is engaged with the proximal ends of the first and second jaws when the driver is moved distally.

11. The medical device of claim 1, wherein the driver is directly engaged with the second ends of the first and second links for movement therewith only when the driver is moved proximally.

12. The medical device of claim 1, wherein the driver includes a distal end for engaging the first and second jaws, the distal end of the driver including a first flange which engages the proximal end of the first jaw and is shaped to permit rotation of the first jaw relative to the first flange while engaged, the distal end of the driver including a second flange which engages the proximal end of the second jaw and is shaped to permit rotation of the second jaw relative to the second flange while engaged.

13. The medical device of claim 1, wherein the driver extends longitudinally to a position located proximal to the second ends of the first and second links.

14. The medical device of claim 1, wherein the first and second jaws are longitudinally slidable between an extended position and a retracted position, and wherein the housing is structured to block rotation of the first and second jaws when in their retracted positions, and the housing is structured to permit rotation of the first and second jaws when in their extended positions.

15. The medical device of claim 1, wherein the first and second links are longitudinally slidable between an extended position and a retracted position, and wherein the housing is structured to block rotation of the first and second links when in their retracted positions, and the housing is structured to permit rotation of the first and second links when in their extended positions.

16. The medical device of claim 1, wherein the housing, the first link, and the first jaw are pivotable relative to each other, and wherein the housing, the second link, and the second jaw are pivotable relative to each other, and wherein the second ends of the first and second links are longitudinally slidable relative to the proximal ends of the first and second jaws, whereby the distance between the second ends and proximal ends determines the rotation of the first and second jaws between a closed configuration and an open configuration.

17. The medical device of claim 1, further comprising an elongate drive wire selectively connected to the driver for longitudinal movement therewith, and further comprising an elongate tubular member selectively connected to the housing.

18. The medical device of claim 17, wherein sufficient proximal translation of the drive wire disconnects the driver from the drive wire and the housing from the elongate tubular member.

19. The medical device of claim 1, further comprising a first link pivot pin that pivotally connects the second end of the first link to the housing, and further comprising a second link pivot pin that pivotally connects the second end of the second link to the housing, and wherein the first link guide surface is defined by opposing first link slots formed in the housing, and wherein the second link guide surface is defined by opposing second link slots formed in the housing, and wherein the opposing first link slots receive opposing ends of the first link pivot pin, and wherein the opposing second link slots receive opposing ends of the second link pivot pin.

20. A method for operating a medical device, the method comprising the steps of:
   providing the medical device comprising a housing, first and second jaws, first and second links, and a driver, wherein the first and second jaws are slidably and pivotally connected to the housing, the first and second links are slidably and pivotally connected to the housing, the first and second links are pivotally attached to the first and second jaws, respectively, and the driver is operatively connected to the first and second jaws;

advancing the driver distally relative to the housing to translate the first and second jaws and the first and second links distally relative to the housing;

limiting the distal translation of the first and second links while further advancing the driver distally relative to the housing to rotate the first and second jaws in a first direction relative to the housing; and retracting the driver proximally to rotate the first and second jaws in a second direction relative to the housing.

21. The method of claim 20, wherein the medical device further comprises an elongated drive wire selectively connected to the driver for longitudinal movement therewith, and further comprising the step of detaching the drive wire from the driver.

* * * * *